United States Patent [19]

Tetzlaff et al.

[11] Patent Number: 5,326,906
[45] Date of Patent: Jul. 5, 1994

[54] PROCESS FOR THE EXTRACTIVE REMOVAL OF PHOSPHO- AND SULFOBETAINES FROM ACIDIC REACTION SOLUTIONS

[75] Inventors: Heribert Tetzlaff, Frankfurt am Main; Matthias Krull, Bad Soden am Taunus; Gernot Kremer, Kelkheim; Christoph Porz, Meckenheim, all of Fed. Rep. of Germany

[73] Assignee: Hoechst Aktiengesellschaft, Frankfurt, Fed. Rep. of Germany

[21] Appl. No.: 819,406

[22] Filed: Jan. 10, 1992

[30] Foreign Application Priority Data

Jan. 10, 1991 [DE] Fed. Rep. of Germany ....... 4100533

[51] Int. Cl.$^5$ .................. C07C 61/00; B01D 35/00
[52] U.S. Cl. .......................... 562/11; 562/12; 562/14; 562/43; 562/101; 562/102; 562/104; 423/387; 423/321.2; 210/660
[58] Field of Search ........ 562/11, 12, 14, 43, 562/101, 102, 104; 548/570; 210/21, 38 R, 39, 40; 423/387, 321 S

[56] References Cited

U.S. PATENT DOCUMENTS

| | | | |
|---|---|---|---|
| 3,318,867 | 5/1967 | Heinz | 548/570 |
| 4,166,942 | 9/1979 | Tunick et al. | 423/387 |
| 4,877,885 | 10/1989 | Ballschuh et al. | 548/570 |
| 4,937,323 | 6/1990 | Garlich et al. | 562/14 |
| 5,008,015 | 4/1991 | Davids et al. | 562/14 |

FOREIGN PATENT DOCUMENTS

| | | | |
|---|---|---|---|
| 0163319 | 12/1985 | European Pat. Off. | 548/570 |
| 1277256 | 9/1968 | Fed. Rep. of Germany | 548/570 |
| 2748366 | 5/1979 | Fed. Rep. of Germany | 562/12 |
| 0417432 | 2/1974 | U.S.S.R. | 562/14 |

Primary Examiner—José G. Dees
Assistant Examiner—Keith MacMillan
Attorney, Agent, or Firm—Connolly and Hutz

[57] ABSTRACT

The ampholytes are extracted from the reaction solution with a liquid cation exchanger which is immiscible with the acidic aqueous reaction solution, where the cation exchanger is dissolved in at least one organic solvent which is immiscible with water and forms an organic phase with the organic solvent. Subsequently the organic phase which is loaded with the ampholyte is separated from the reaction solution, and then the ampholytes are back-extracted from the organic phase with aqueous solvents. The product losses in the process are low, and the residual salt content is very low.

18 Claims, No Drawings

PROCESS FOR THE EXTRACTIVE REMOVAL OF PHOSPHO- AND SULFOBETAINES FROM ACIDIC REACTION SOLUTIONS

The invention relates to a process for the extractive removal of ampholytes based on phospho- and sulfobetaines from their acidic aqueous reaction solutions. Ampholytes are compounds which carry both anionic and cationic groups.

Examples of ampholytes of industrial interest are phosphobetaines of the formula I

$$R^1R^2YN^+ - CHR^3 - PO_3M^-  \quad (I),$$

in which $R^1$ and $R^2$ are, independently of one another, hydrogen, $C_1$–$C_{20}$-alkyl, $C_2$–$C_{20}$-alkenyl, alkylphenyl with 1 to 20 carbon atoms in the alkyl chain or $C_1$–$C_{20}$-alkyl, preferably $C_1$–$C_{12}$-alkyl, $C_2$–$C_{12}$-alkenyl, alkylphenyl with 1 to 12 carbon atoms in the alkyl chain or $C_1$–$C_{12}$-acyl, Y is hydrogen or $CHR^3$–$PO_3M$, M is hydrogen, $C_1$–$C_4$-alkyl or a cation, preferably ammonium or an alkali metal cation, and $R^3$ is hydrogen, benzyl, $C_1$–$C_{10}$-alkyl, preferably $C_1$–$C_5$-alkyl or $PO_3M^-$. It is also possible for the phosphobetaines of the formula I to be a polyamine in which $R^2$ is $[(CH_2)_nNZ]_xZ$ where n is numbers from 1 to 3 and x is numbers from 2 to 10, and Z can have the meaning described above for $R^1$ or Y.

The ampholytes of the formula I can be obtained in a straightforward manner by reacting amines of the formula $NHR^1R^2$ with aldehydes $R^3CHO$, where $R^1$, $R^2$ and $R^3$ have the same meaning as above, and phosphorous acid in a Mannich reaction (K. Moedritzer, R. R. Irani, J. Org. Chem. 1966, 31, 1603). In this case, a 2–3 molar excess of mineral acid such as, for example, hydrochloric or sulfuric acid is added to prevent the oxidation of the phosphorous acid and to achieve high yields with short reaction times. The phosphonic acids which are formed can subsequently, where appropriate, be converted into their metal salts by neutralization with bases.

The synthesis usually results in the phosphobetaines in solutions which have a high salt content and may additionally contain precursors too.

According to the not prior-published German patent application P 4001420.7, it is possible to isolate the aminomethylenephosphonic acids of the formula I by precipitation and, where appropriate, reprecipitation several times from suitable solvents. Thus, allylaminobis(methylenephosphonic acid), in which $R^1$ is $CH_2$—$CH$=$CH_2$, Y is $CHR^3$—$PO_3HM$, $R^2$ and $R^3$ are each hydrogen, is isolated by extracting the sulfuric acid from the reaction mixture with acetone, but large amounts of acetone are necessary (12×3 l acetone for 100 g of substance) and considerable amounts of product are lost. Furthermore, partial neutralization of the reaction solution is necessary in this process and results in a residual sulfate content of more than 6% by weight in the product.

α-Aminomethylenephosphonic acids of the formula I are used, for example, as builders and cobuilders in detergents (P 4001420.7) as anticorrosion agents (DE-A-22 30 832 and DE-A-22 31 206) and in flame-resistant fabrics (JP-A-48012475). In addition, they are employed as complexing reagents and for crystal modification to prevent scale in saline waters and in drilling for oil (U.S. Pat. No. 4,707,306). For certain applications, moreover, the reactive substances must be prepared in pure form, i.e. without precursors such as, for example, residues of formaldehyde, without by]products and, in particular, free of salts.

A similar class of substances is represented by the sulfobetaines of the formulae II and III

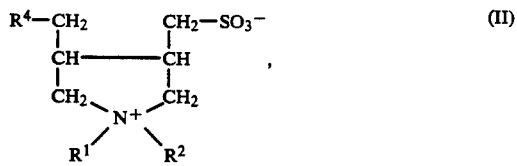

$$R^1(R^2)_2N^+ - CH_2 - CHR^5 - CH_2 - SO_3^- \quad (III)$$

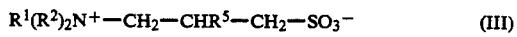

in which $R^1$ and $R^2$ are, independently of one another, hydrogen, $C_1$–$C_{20}$-alkyl, $C_2$–$C_{20}$-alkenyl, alkylphenyl with 1 to 20 carbon atoms in the alkyl chain or $C_1$–$C_{20}$-acyl, preferably $C_1$–$C_{12}$-alkyl, $C_2$–$C_{12}$-alkenyl, alkylphenyl with 1 to 12 carbon atoms in the alkyl chain or $C_1$–$C_{12}$-acyl, in which $R^{14}$ is hydrogen, $SO_2H$, $SO_2M$, where M is ammonium or an alkali metal cation or a radical of the formula $SO_2$—$R^6$, in which $R^5$ is hydrogen, hydroxyl, $SO_2H$, $SO_3H$ or $SO_2R^6$, where $R^6$ is a radical of the group comprising $C_1$–$C_{30}$-alkyl, preferably $C_1$–$C_{22}$-alkyl, in particular methyl or ethyl or $C_{18}$–$C_{20}$-alkyl which is optionally substituted by halogens, preferably fluorine or chlorine, hydroxyl or amino groups, and/or where the alkyl chain can be interrupted at any desired point by the group —CO—O—, —CO—NH— or —NH—.

When prepared from, for example, diallyldimethylammonium chloride and sulfite as described in EP-A-163 319, sulfobetaines of the formula II ($R^1=R^2=-CH_3$, $R^4=H$ or $SO_2H$) crystallize from the solution in hydrochloric acid with about 5% sodium chloride. In this case too isolation free of salts and by-products is required for certain applications.

DE-B-12 77 256 discloses a process for the extraction of amino acids from dilute aqueous solutions at pH 4 to 10 with sodium dinonylnaphthalenesulfonate, where the extract is back-extracted with aqueous solutions of strong organic bases or the salts thereof. A review of the ion exchanger properties of dinonylnaphthalenesulfonic acid is given by E. Hoegfeldt et al. (Chem. Scr. 1981, 18, 13).

The object of the present invention is to provide a process, which is less elaborate than that of the prior art and entails minimal losses, for the extractive removal of ampholytes based on phospho- and sulfobetaines from their acidic aqueous reaction solutions, where the residual salt content in the product should be as low as possible.

It has now been found, surprisingly, that ampholytes based on phospho- and sulfobetaines, especially of the abovementioned formulae (I), (II) and (III), are extracted from the reaction solution with a liquid cation exchanger which is immiscible with the acidic aqueous reaction solution, where the cation exchanger is dissolved in at least one organic solvent which is immiscible with water and forms an organic phase with the organic solvent, subsequently the organic phase which is loaded with the ampholyte is separated from the reaction solution, and then the ampholytes are back-extracted from the organic phase with aqueous solvents.

The extremely hydrophilic ampholytes are in this process subjected to, expediently multistage, in particular countercurrent, extraction from the acidic aqueous reaction solution with the hydrophobic cation exchanger in a conventional extraction apparatus. The hydrophobic organic phase which is loaded with the ampholyte is subsequently separated from the aqueous phase and subjected to, expediently likewise multistage, countercurrent back-extraction with hot water in another extraction system.

It is particularly advantageous for carrying out the process according to the invention that the acidic aqueous reaction solution has a pH of less than or equal to 4, preferably less than or equal to 2. Cation exchangers which are particularly used are hydrophobic strong organic acids, preferably aromatic carboxylic or sulfonic acids, which are substituted by alkyl radicals. It is particularly advantageous to use as cation exchangers aromatic carboxylic and sulfonic acids which contain 1 to 3 carboxyl or sulfo groups, preferably one carboxyl or sulfo group, per molecule and 1 to 4 alkyl chains, where the number of carbon atoms in the carboxylic or sulfonic acid totals 10 to 60, preferably 20 to 40, in particular 25 to 35, or mixtures of these carboxylic or sulfonic acids. The cation exchanger is dissolved in one or more aliphatic or aromatic hydrocarbons which are immiscible with water or in one or more aliphatic or aromatic partially halogenated or perhalogenated hydrocarbons which are immiscible with water, where halogen is fluorine and/or chlorine, or in mixtures thereof. Preferably used are kerosine, paraffins, alkylaromatics or halogenated hydrocarbons, whose solubility in water is less than 1% by weight at 20° C. The concentration of the cation exchanger in the organic solvent can be 10 to 90% by weight, preferably 40 to 60% by weight.

The extractive removal of the ampholytes I to III from their acidic solutions, as well as the back-extraction with water, are carried out most economically by multi-stage, continuous or intermittent continuous countercurrent extraction. Suitable apparatus for carrying out the extractions is any conventional extraction apparatus, such as, for example, columns, mixer settlers or centrifugal extractors.

In a preferred embodiment of the process, the reaction mixture (S) is subjected to multistage countercurrent extraction with 50% by weight dinonylnaphthalenesulfonic acid in kerosine (X). The extraction takes place at between 0° and 100° C., preferably between 10° and 35° C. The S:X ratio by volume is between 1:10 and 10:1. The mineral acid which is free of product and runs out at one end of the extraction system can be returned, after concentration, to the reaction stage.

The extract which is loaded with the ampholyte and runs out of the other end of the extraction system is passed to another extraction system in which the ampholytes according to the invention are back-extracted in a preferred variant of the process by treatment with hot water. Preferably multistage countercurrent back-extraction with water (R) is carried out. The temperatures in the back-extraction column are between 40° and 100° C., preferably between 60° and 100° C., and the X:R ratio by volume is between 1:10 and 10:1. The extract phase is subsequently returned to the extraction stage. The compounds can be obtained in crystalline form after evaporation of the aqueous back-extract and, where appropriate, addition of suitable solvents, such as, for example, alcohols, ketones or mixtures thereof, to the residue from evaporation.

Thus, surprisingly, no displacement reagents such as the amines and ammonium salts used in DE-C 12 77 256 are required for the back-extraction. It is therefore possible for the solution of the cation exchanger to be reused immediately for the extraction, i.e. without previous processing.

The process is explained in detail by means of the following examples.

EXAMPLE 1

A reaction solution containing 32% by weight of allylaminobismethylenephosphonic acid in concentrated sulfuric acid is subjected to 10-stage countercurrent extraction with 6 times the amount of 50% by weight dinonylnaphthalenesulfonic acid in kerosine in a laboratory mixer settler. During this, 99% of the phosphonic acid are transferred into the organic phase. The organic extract phase is subsequently back-extracted, likewise in the laboratory mixer settler, at 90° C. with 1/6 of the amount of water, when the phosphonic acid is transferred virtually quantitatively into the aqueous phase. The remaining organic phase can be reused for the extraction. After evaporation of the water at 40° C./1 mbar, the remaining mass is recrystallized with 3 times the amount of ethanol, filtered off in vacuo and dried. The yield of phosphonic acid, based on the original amount in the reaction solution, is 85%, and the sulfate content is 1.0% by weight. The yield can be increased further by reusing the ethanol employed for the recrystallization.

EXAMPLE 2

A reaction solution in sulfuric acid containing 35% by weight of diallylaminomethylenephosphonic acid (phosphobetaine) is subjected to continuous countercurrent extraction in an oscillating plate column (Karr type, 3 m high, diameter 50 mm) with the same amount of dinonylnaphthalenesulfonic acid (50% by weight in kerosine) at room temperature. 90% of the phosphobetaine are transferred into the organic extract phase during this. The organic extract is subsequently pumped into a second oscillating plate column of the same design where it is continuously back-extracted with the same amount of water. The phosphobetaine which is transferred into the aqueous phase during this is obtained as a yellowish oil by evaporation in vacuo (40° C., 1 mbar). The total yield of diallylaminomethylenephosphonic acid is 85% of the initial amount.

EXAMPLE 3

A reaction solution in hydrochloric acid (pH 2) containing 30% by weight of the sulfobetaine II ($R^1=R^2=CH_3$, $R^4=SO_2-CH_2-COOH$) is subjected to continuous 8-stage countercurrent extraction with the same amount of dinonylnaphthalenesulfonic acid (50% by weight in kerosine) in a laboratory mixer settler at room temperature. 95% of the sulfobetaine are transferred into the organic phase during this. The organic extract is subsequently conveyed continuously into a second laboratory mixer settler where the sulfobetaine II is back-extracted (continuously, 8 stages) with the same amount of water at 60° C. The sulfobetaine is transferred virtually quantitatively into the aqueous phase during this, and the organic phase is returned to the extraction stage. The back extract is concentrated at 40° C., 1 mbar, until a viscous mass remains, and the sulfobetaine is precipitated therefrom by adding cold ethanol. Filtration and drying (40° C., vacuum oven) result in the sulfobetaine in a yield of 80% with a residual chloride content of 0.74%.

These examples show that the rates of product loss in the process according to the invention are relatively low and the residual sulfate content is distinctly less than that disclosed in the prior art.

We claim:

1. A process for the extractive removal of ampholytes based on phospho- and sulfobetaines from their acidic aqueous reaction solutions, which comprises the ampholytes being extracted from the reaction solution with a liquid cation exchanger which is immiscible with the acidic aqueous reaction solution, where the cation exchanger is dissolved in at least one organic solvent which is immiscible with water and forms an organic phase with the organic solvent, subsequently the organic phase which being loaded with the ampholyte being separated from the reaction solution, and then the ampholytes being back-extracted from the organic phase with aqueous solvents.

2. The process as claimed in claim 1, wherein the acidic aqueous reaction solution has a pH of less than or equal to 4, preferably less than or equal to 2.

3. The process as claimed in claim 1, wherein cation exchangers based on hydrophobic strong organic acids, are used.

4. The process as claimed in claim 1, wherein aromatic carboxylic and sulfonic acids which contain 1 to 3 carboxyl or sulfo groups, per molecule and 1 to 4 alkyl chains, where the number of carbon atoms in the carboxylic or sulfonic acid totals 10 to 60, or mixtures of these carboxylic or sulfonic acids are used as cation exchangers.

5. The process as claimed in claim 1, wherein the cation exchanger is dissolved in an organic solvent based on one or more aliphatic or aromatic hydrocarbons which are immiscible with water or in one or more aliphatic or aromatic partially halogenated or perhalogenated hydrocarbons which are immiscible with water, where halogen is fluorine and/or chlorine, or in mixtures thereof.

6. The process as claimed in claim 1, wherein the extraction is carried out at temperatures between 0° and 100° C.

7. The process as claimed in claim 1, wherein multi-stage, extraction is carried out.

8. The process as claimed in claim 1, wherein the ampholyte is back-extracted from the cation exchanger with aqueous solvents at 40° to 100° C., and then the resulting ampholyte is optionally crystallised.

9. The process as claimed in claim 1, wherein the concentration of the cation exchanger in the organic solvent is 10 to 90% by weight.

10. The process as claimed in claim 1, wherein the phosphobetaines have the formula I $$R^1R^2YN^+ - CHR^3 - PO_3M' \qquad (I),$$

in which $R^1$ and $R^2$ are, independently of one another, hydrogen, $C_1-C_{20}$-alkyl, $C_2-C_{20}$-alkenyl, alkylphenyl with 1 to 20 carbon atoms in the alkyl chain or $C_1-C_{20}$-acyl, $C_2-C_{12}$-alkenyl, aikylphenyl with 1 to 12 carbon atoms in the alkyl chain or $C_1-C_{12}$-acyl, or in which $R^2$ is $[(CH_2)_nNZ]_xZ$ where n is numbers from 1 to 3 and x is numbers from 2 to 10 and Z can have the meaning of $R^1$ or Y, Y is hydrogen or $CHR^3-PO_3HM$, M is hydrogen, $C_1-C_4$-alkyl or a cation, and $R^3$ is hydrogen, benzyl or $C_1-C_{10}$-alkyl.

11. A process as claimed in claim 1, wherein the sulfobetaines have the formula II or III

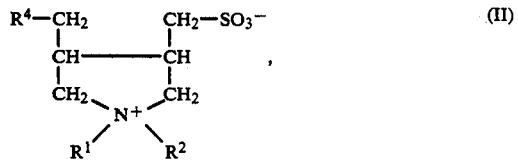

$$R^1(R^2)_2N^+ - CH_2 - CHR^5 - CH_2 - SO_3^- \qquad (III)$$

in which $R^1$ and $R^2$ are, independently of one another, hydrogen, $C_1-C_{20}$-alkyl, $C_2-C_{20}$-alkenyl, alkylphenyl with 1 to 20 carbon atoms in the alkyl chain or $C_1-C_{20}$-acyl, $C_2-C_{12}$-alkenyl, alkylphenyl with 1 to 12 carbon atoms in the alkyl chain or $C_1-C_{12}$-acyl, in which $R^4$ is hydrogen, $SO_2H$, $SO_2M$, where M is ammonium or an alkali metal cation or a radical of the formula $SO_2-R^5$, in which $R^5$ is hydrogen, hydroxyl, $SO_2H$, $SO_3H$ or $SO_2-R^6$, where $R^6$ is substituted or unsubstituted $C_1-C_{30}$-alkyl.

12. The process as claimed in claim 1, wherein the acidic aqueous reaction solution has a pH of less than or equal to 2.

13. The process as claimed in claim 2, wherein a cation exchanger based on a hydrophobic strong organic acid is used.

14. The process as claimed in claim 1, wherein said cation exchanger is an aromatic carboxylic or sulfonic acid which contains 1 to 3 carboxy or sulfo groups per molecule.

15. The process as claimed in claim 4, wherein said cation exchanger contains one carboxyl or sulfo group, and wherein the number of carbon atoms in the carboxylic or sulfonic acid totals 20 to 40.

16. The process as claimed in claim 1, wherein the extraction is carried out at a temperature between 10° and 35° C. and is carried out as a multistage, countercurrent extraction, and wherein the concentration of the cation exchanger in the organic solvent is 40 to 60% by weight.

17. The process as claimed in claim 10, wherein $R^1$ and $R^2$ are $C^1-C_{12}$-alkyl, M is ammonium or an alkali metal cation, and $R^3$ is $C_1-C_5$-alkyl.

18. The process as claimed in claim 11, wherein $R^1$ and $R^2$ are $C_1-C_{12}$-alkyl, and wherein $R^6$ is $C_{18}-C_{20}$-alkyl which is optionally substituted by halogens, hydroxyl or amino groups, and/or where the alkyl chain is optionally interrupted at any point by the group $-CO-O-$, $-CO-NH-$ or $-NH-$.

* * * * *